United States Patent [19]
Celia

[11] Patent Number: 5,976,616
[45] Date of Patent: Nov. 2, 1999

[54] POLYURETHANE FOAM MATERIALS WITH SKIN CONDITIONING ADDITIVES

[75] Inventor: Wayne Celia, Paramus, N.J.

[73] Assignee: H.H. Brown Shoe Technologies, Inc., Fairlawn, N.J.

[21] Appl. No.: 09/165,899

[22] Filed: Oct. 2, 1998

[51] Int. Cl.[6] .............................. B65B 33/00; B05D 5/00; C08J 9/40
[52] U.S. Cl. .......................... 427/155; 427/244; 424/404; 424/443; 424/422; 521/54; 521/65; 521/918

[56] References Cited

U.S. PATENT DOCUMENTS

| | | |
|---|---|---|
| 3,839,138 | 10/1974 | Kyle et al. . |
| 4,339,550 | 7/1982 | Palinczar et al. . |
| 4,985,467 | 1/1991 | Kelly et al. . |
| 5,762,946 | 6/1998 | Gueret . |
| 5,763,335 | 6/1998 | Hermann . |

*Primary Examiner*—Morton Foelak
*Attorney, Agent, or Firm*—Lerner, David, Littenberg, Krumholz & Mentlik, LLP

[57] ABSTRACT

Polyurethane foam pads for use in the topical care and treatment of the skin are disclosed. The polyurethane pads are formed from a polymerized combination of an aqueous mixture having at least one skin conditioning agent (such as Vitamin E or aloe) and a quantity of hydrophilic urethane prepolymer. The skin conditioning agents are incorporated directly into the cell structure of the polyurethane foam pad and are readily released when contacted with water.

9 Claims, No Drawings

POLYURETHANE FOAM MATERIALS WITH SKIN CONDITIONING ADDITIVES

The invention relates to hydrophilic polyurethane foam pads for the topical treatment and care of the skin. More particularly the present invention relates to hydrophilic polyurethane foam pads which contain skin conditioning agents.

BACKGROUND OF THE INVENTION

It has been known to impregnate foam pads with volatile agents for the purpose of slowly releasing these agents over a period of time. U.S. Pat. No. 4,339,550, for example, describes a foam product impregnated with volatile, active materials such as medicaments, perfumes, deodorants, germicides, pesticides, and disinfecting and sterilizing agents. The agents are incorporated into the cell structure of hydrophilic polyurethane foam during the foaming process. However, do to the volatility of these agents, techniques must be employed to prevent the agents from being rapidly released. These techniques include using an irreversible chemical reaction which causes the volatile material to become an intricate part of the foam structure; controlling the pore size of the polyurethane foam structure to permit only a portion of the volatile material to be released; and using a variety of controlled release ingredients that aid in producing in a sustained releases.

It is also known to incorporate nonvolatile agents into foam pads for the care and topical treatment of the skin. U.S. Pat. No. 5,762,946 describes a foam pad having a skin conditioning agent, in powder form, arranged at the center of a sheet of foam. The sheet is superimposed with another sheet such that the powdered product is incorporated between the two sheets. U.S. Pat. No. 5,762,946 also describes a foam pad in which the skin conditioning agents are incorporated into the foam pads after the foam has been produced by impregnating the polymerized foam products with a solution containing the skin conditioning agent and then dehydrating the foam product. However, adding the non-volatile agents into the post-polymerization foam structure permits the incorporation of the skin conditioning agents only into the open cell structure of the foam and prevents any substantial retention of the additive or long lasting release benefit.

SUMMARY OF INVENTION

The present invention is directed to hydrophilic polyurethane foam pads having skin condition agents disposed therein. The hydrophilic foam pads of the present invention are formed from a polymerized combination of an aqueous mixture with a predetermined quantity of hydrophilic urethane prepolymer. The skin conditioning agents are added directly to the prepolymerization aqueous mixture and are thus incorporated directly into the cell structure of the foam pad. The introduction of the skin conditioning additives into the foam matrix during polymerization produces a foam structure having unique properties such that when wetted, the polyurethane pads quickly will release the skin conditioning agents for application to skin, but will retain a substantial amount of additive for additional application.

The present invention is also directed to a method for making a cosmetic pad in accordance with the present invention which includes the steps for forming the composite material by:

a) metering and mixing an aqueous mixture having at least one skin conditioning agent and adequate water, with a predetermined ratio of hydrophilic urethane prepolymer to provide a polymerizing mixture for forming the foam layer of the composite material;

b) depositing the polymerizing mixture on releasable bottom paper disposed on a moveable carrier and covering the upper surface of the polymerizing mixture with releasable top paper as the polymerizing mixture is moved with the carrier;

c) advancing the polymerizing mixture in the top and bottom release paper by moving the carrier and sizing the foam layer being formed to the desired thickness until it is tack free;

d) sequentially removing the top and bottom releasable paper and simultaneously drying the sized and formed foam layer to remove residual moisture.

DETAILED DESCRIPTION

The hydrophilic foam pads of the present invention are formed by polymerizing an aqueous mixture having one or more skin conditioning agents with a predetermined quantity of a hydrophilic urethane prepolymer binder so that the polymerization of the polyurethane foam forms a matrix binder for one or more skin conditioning agents. The skin condition agents are incorporated directly into the cell structure of the foam pads and remain there until the foam pads are wetted or contacted with a sufficient moisture content. Once the pads are wetted or contacted with a sufficient moisture content, the skin conditioning agents are released from the matrix and diffuse toward the surface of the pad for contact with the skin.

The formation of the cosmetic pads in accordance with the present invention is done by metering and mixing an aqueous mixture including adequate water and at least one skin conditioning agent with a predetermined ratio of hydrophilic urethane prepolymer to provide a polymerizing mixture. The aqueous mixture includes water which is present in amounts from about 15 to about 95% by weight. The concentration of the skin conditioning agents in the aqueous phase is from about 0.5% to about 3.5%.

The skin conditioning agents of the present invention are nonvolatile agents and include vitamins, mineral salts, trace elements, plant and animal extracts, proteins, enzymes, and other agents which have therapeutic benefits for the skin. By the term "nonvolatile" it is meant that the skin conditioning agents have a high boiling or subliming temperature at normal pressures and thus do not readily evaporate at normal temperatures and pressures.

The skin conditioning agents may first be dispersed into a typical surfactant material in a prepared premix. Surfactants may be used in the aqueous solution to increase the concentration of the skin conditioning agents in the aqueous mixture. The surfactants are preferably present in amounts of about 0.5 to about 3.5% by weight of the aqueous mixture. The surfactants may be prepared from nonionic polyethylene and polypropylene oxides such as BASF surfactant available under the trademark "PLURONIC". Other components may be added to the aqueous mixture to increase the concentration of the skin conditioning agent, such as citric acid which acts as a buffer for reducing the pH of the water component.

The aqueous mixture may further consist of various combinations of other components without departing from the scope of the present invention, including, for example, soaps, bactericides and fungicides. Bactericides are provided in the commercial marketplace by a myriad of suppliers for controlling bacterial and fungal growth. One preferred material is supplied by Lauricidin Co. of Galena, Ill. 61036, under the trademark "LAURICIDIN".

The hydrophilic urethane prepolymer component of the present invention is available in the commercial marketplace. Suitable prepolymers will be readily recognized by those of ordinary skill in the art and are described in prior art U.S. Pat. Nos. 4,137,200; 4,209,605; 3,805,532; 2,999,013 and general procedures for the preparation and formation of such prepolymers can be found in Polyurethane's Chemistry and Technology by J. H. Suanders and K. C. Frisch published by John Wiley & Sons, New York, N.Y., at Vol. XVI Part 2, High Polymer Series, "Foam Systems", pages 7–26, and "Procedures for the Preparation of Polymers", pages 26 et seq. One preferred prepolymer for use in the present invention is Bipol 6 available from Mace Adhesives and Coatings. The hydrophilic urethane prepolymer is present in amount of about 20 to about 50% by weight of the total composition.

As will be appreciated by those skilled in the art, the cosmetic pads of the present invention can be formed to have any desired thickness and shape. After blending and mixing the combination of the aqueous mixtures and hydrophilic urethane prepolymer, the polymerizing foam pad composition is preferably deposited on a releasable bottom paper on a movable carrier. The upper surface of the polymerizing composition is then covered with a releasable top paper and advanced along the moveable carrier for sizing of the foam to the desired thickness and until the foam is tack free. The top and bottom releasable paper are sequentially removed. When polymerization is complete, residual water may be driven off by drying the foam in a drying unit at a temperature of about 200° F.

Preferably the foam pads of the present invention have a thickness of about 1 mm to about 40 mm. The foam pad may initially be formed into large blocks which are then cut into any desired shape.

EXAMPLES

Example 1

| Ingredients | Percent by Weight |
| --- | --- |
| Water | 93.06% |
| Surfactant (BASF F88 Pluronic) | 1.58% |
| Burgess Clay (Wolastinite) | 4.15% |
| Bactericide | .28% |
| Vitamin E | 1.23% |

This aqueous mixture was then metered with the hydrophilic prepolymer at a ratio of 2 parts aqueous to 1 part polymer by weight and dispensed onto a moving casting liner. After polymerization, the web is sized and compressed to achieve the target thickness.

Example 2

| Ingredients | Percent by Weight |
| --- | --- |
| Water | 93.06% |
| Surfactant (BASF F88 Pluronic) | 1.58% |
| Burgess Clay (Wolastinite) | 4.15% |
| Bactericide | .28% |
| Vitamin A | 1.23% |

This aqueous mixture was then metered and mixed with a hydrophilic prepolymer in a ratio of 3.2 parts to 1 part by weight. After polymerization the web is sized and compressed to desired thickness.

Example 3

| Ingredients | Percent by Weight |
| --- | --- |
| Water | 92.11% |
| Surfactant (BASF F88 Pluronic) | 1.58% |
| Surfactant (BASF L62 Pluronic) | 1.25% |
| Burgess Clay (Wolastinite) | 4.15% |
| Bactericide | .28% |
| Aloe | .93% |

This aqueous mixture was then metered and mixed with a hydrophilic prepolymer in a ratio of 2.7 parts to 1 by weight. After polymerization the web is sized and compressed to desired thickness.

The embodiments described above should provide adequate details of the invention. However, it should be noted by those skilled in the art that the disclosures herein are exemplary only and that various other alternatives, adaptations and modifications may be made within the scope of the present invention. Accordingly, the present invention is not limited by the specific embodiments as illustrated.

I claim:

1. A hydrophilic polyurethane foam composition for use as a pad in the topical treatment of the skin comprising the reaction product of:

an aqueous mixture including water which is present in an amount from about 15 to about 95% by weight of the aqueous mixture and at least one skin conditioning agent present in an amount from about 0.5 to about 3.5% by weight of the aqueous mixture; and a hydrophilic polyurethane prepolymer of from about 20 to about 50% by weight of the total composition.

2. The composition of claim 1 wherein the aqueous mixture further includes at least one surfactant present in an amount of from about 0.5 to about 5% by weight of the aqueous mixture.

3. The composition of claim 1 wherein the skin conditioning agent is selected from the group consisting of vitamins, mineral salts, trace elements, plant extracts, animal extracts, proteins, and enzymes.

4. The composition of claim 1 wherein the skin conditioning agent is vitamin E.

5. The composition of claim 1 wherein the skin conditioning agent is vitamin A.

6. The composition of claim 1 wherein the skin conditioning agent is aloe.

7. The composition of any one of the preceding claims wherein the aqueous mixture further includes one or more additives selected from the group consisting of soaps, bactericides, or fungicides.

8. A method for producing a foam pad having one or more skin conditioning agents comprising the steps of:

a) forming an aqueous mixture having at least one skin conditioning agent and water in a quantity sufficient for the mixture;

b) metering a predetermined amount of hydrophilic urethane prepolymer with said aqueous mixture to form a foam layer of composite material, and c) converting the foam layer into a desired shape for use.

9. A method for producing foam pads having one or more skin conditioning agents comprising the steps of:

a) metering and mixing an aqueous mixture having at least one skin conditioning agent and adequate water, with a predetermined ratio of hydrophilic urethane prepolymer to provide a polymerizing mixture for forming the foam layer of the composite material;

b) depositing the polymerizing mixture on releasable bottom paper disposed on a moveable carrier and covering the upper surface of the polymerizing mixture with releasable top paper as the polymerizing mixture is moved with the carrier;

c) advancing the polymerizing mixture in the top and bottom release paper by moving the carrier and sizing the foam layer being formed to the desired thickness until it is tack free;

d) sequentially removing the top and bottom releasable paper and simultaneously drying the sized and formed foam layer to remove residual moisture.

\* \* \* \* \*

UNITED STATES PATENT AND TRADEMARK OFFICE
CERTIFICATE OF CORRECTION

PATENT NO. : 5,976,616

DATED : November 2, 1999

INVENTOR(S) : Celia

It is certified that error appears in the above-identified patent and that said Letters Patent is hereby corrected as shown below:

On the cover page after "[73] Assignee: H.H. Brown Shoe Technologies, Inc.," insert --d/b/a/ Dicon Technologies--.

Signed and Sealed this

Eighteenth Day of July, 2000

*Attest:*

Q. TODD DICKINSON

*Attesting Officer*      *Director of Patents and Trademarks*

(12) EX PARTE REEXAMINATION CERTIFICATE (7185th)
United States Patent
Celia

(10) Number: US 5,976,616 C1
(45) Certificate Issued: Nov. 24, 2009

(54) POLYURETHANE FOAM MATERIALS WITH SKIN CONDITIONING ADDITIVES

(75) Inventor: Wayne Celia, Paramus, NJ (US)

(73) Assignee: H. H. Brown Shoe Technologies Inc., Fair Lawn, NJ (US)

Reexamination Request:
No. 90/009,163, May 30, 2008

Reexamination Certificate for:
Patent No.: 5,976,616
Issued: Nov. 2, 1999
Appl. No.: 09/165,899
Filed: Oct. 2, 1998

Certificate of Correction issued Jul. 18, 2000.

(51) Int. Cl.
*A61K 8/02* (2006.01)

(52) U.S. Cl. .................. 427/155; 424/404; 424/442; 424/443; 427/244; 521/54; 521/65; 521/918

(58) Field of Classification Search .................. None
See application file for complete search history.

(56) References Cited

U.S. PATENT DOCUMENTS

| 2,956,310 A | | 10/1960 | Roop et al. |
| 4,216,177 A | | 8/1980 | Otto |
| 4,344,930 A | | 8/1982 | MacRae et al. |
| 4,369,180 A | * | 1/1983 | Mihalovits .................. 514/21 |
| 5,372,805 A | | 12/1994 | Finkel et al. |

\* cited by examiner

*Primary Examiner*—Dwayne C Jones

(57) ABSTRACT

Polyurethane foam pads for use in the topical care and treatment of the skin are disclosed. The polyurethane pads are formed from a polymerized combination of an aqueous mixture having at least one skin conditioning agent (such as Vitamin E or aloe) and a quantity of hydrophilic urethane prepolymer. The skin conditioning agents are incorporated directly into the cell structure of the polyurethane foam pad and are readily released when contacted with water.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 8 and 9 are determined to be patentable as amended.

Claim 2–7, dependent on an amended claim, are determined to be patentable.

New claims 10 and 11 are added and determined to be patentable.

1. A hydrophilic polyurethane foam composition for use as a pad in the topical treatment of the skin comprising the reaction product of:
    an aqueous mixture including water which is present in an amount from about 15 to about 95% by weight of the aqueous mixture and at least one skin conditioning agent present in an amount from [about] 0.5 to [about] 3.5% by weight of the aqueous mixture; and
    a hydrophilic polyurethane prepolymer of from about 20 to about 50% by weight of the total composition.

8. A method for producing a foam pad having one or more skin conditioning agents comprising the steps of:
    a) forming an aqueous mixture having at least one skin conditioning agent *in an amount from 0.5 to 3.5% by weight of the aqueous mixture* and water in a quantity sufficient for the mixture;
    b) metering a predetermined amount of hydrophilic urethane prepolymer with said aqueous mixture to form a foam layer of composite material, and
    c) converting the foam layer into a desired shape for use.

9. A method for producing foam pads having one or more skin conditioning agents comprising the steps of:
    a) metering and mixing an aqueous mixture having at least one skin conditioning agent *in an amount from 0.5 to 3.5% by weight of the aqueous mixture* and adequate water, with a predetermined ratio of hydrophilic urethane prepolymer to provide a polymerizing mixture for forming the foam layer of the composite material;
    b) depositing the polymerizing mixture on releasable bottom paper disposed on a moveable carrier and covering the upper surface of the polymerizing mixture with releasable top paper as the polymerizing mixture is moved with the carrier;
    c) advancing the polymerizing mixture in the top and bottom release paper by moving the carrier and sizing the foam layer being formed to the desired thickness until it is tack free;
    d) sequentially removing the top and bottom releasable paper and simultaneously drying the sized and formed foam layer to remove residual moisture.

*10. The composition of claim 1, wherein the at least one skin conditioning agent is present in an amount of about 1.23% by weight of the aqueous mixture.*

*11. The composition of claim 1, wherein the at least one skin conditioning agent is present in an amount of about 0.93% by weight of the aqueous mixture.*

* * * * *